(12) United States Patent
Hsu et al.

(10) Patent No.: US 11,149,239 B2
(45) Date of Patent: Oct. 19, 2021

(54) METHOD FOR PRODUCING LOW-SUGAR VEGETABLE AND FRUIT ENZYME PRODUCT

(71) Applicant: Greenyn Biotechnology Co., Ltd, Taichung (TW)

(72) Inventors: Pang-Kuei Hsu, Taichung (TW); Yu-Cheng Lin, Taichung (TW); Chia-Feng Wu, Taichung (TW)

(73) Assignee: Greenyn Biotechnology Co., Ltd, Taichung (TW)

( * ) Notice: Subject to any disclaimer, the term of this patent is extended or adjusted under 35 U.S.C. 154(b) by 38 days.

(21) Appl. No.: 16/400,557

(22) Filed: May 1, 2019

(65) Prior Publication Data

US 2019/0338227 A1 Nov. 7, 2019

(30) Foreign Application Priority Data

May 3, 2018 (TW) .................................. 107115133
Apr. 29, 2019 (TW) .................................. 108114906

(51) Int. Cl.
| | | |
|---|---|---|
| *C12G 3/02* | (2019.01) | |
| *C12G 3/08* | (2006.01) | |
| *C12N 1/18* | (2006.01) | |
| *C12N 1/20* | (2006.01) | |
| *C12G 3/024* | (2019.01) | |

(52) U.S. Cl.
CPC .............. *C12G 3/024* (2019.02); *C12G 3/08* (2013.01); *C12N 1/18* (2013.01); *C12N 1/20* (2013.01); *C12G 2200/05* (2013.01)

(58) Field of Classification Search
CPC . C12G 3/02; C12G 3/024; C12N 1/18; C12N 1/20
See application file for complete search history.

(56) References Cited

U.S. PATENT DOCUMENTS

2015/0315533 A1* 11/2015 Keller ...................... A23L 2/38 426/15
2017/0342358 A1* 11/2017 Cheng .................... C12M 29/06

FOREIGN PATENT DOCUMENTS

CN          107668725 A  *  2/2018  .......... A23L 33/135

OTHER PUBLICATIONS

Google translation of CN 107668725 (Year: 2018).*
Mamlouk, D., Gullo, M., "Acetic Acid Bacteria: Physiology and Carbon Sources Oxidation", 2013, Indian Journal of Microbiology 53(4), pp. 377-384 (Year: 2013).*
Ghosh, S., Chakraborty, R, Chatterjee, G., Raychaudhuri, U., "Study on fermentation conditions of palm juice vinegar by response surface methodology and development of a kinetic model", 2012, Braz. J. Chem. Eng., vol. 29, n.3, pp. 461-472 (Year: 2012).*
Hofvendahl, K., Hahn-Hagerdal, B., "Factors affecting the fermentative lactic acid production from renewable resources", 2000, Enzyme and Microbial Technology, vol. 26, pp. 87-107 (Year: 2000).*

* cited by examiner

*Primary Examiner* — Jeffrey P Mornhinweg
*Assistant Examiner* — Kelly P Kershaw
(74) *Attorney, Agent, or Firm* — Muncy, Geissler Olds & Lowe, P.C.

(57) ABSTRACT

This invention disclosed a method for preparing low-sugar vegetable and fruit enzyme product comprising obtaining a fruit or/and vegetable as a material; fermenting the material for at least three times sequentially, and producing an enzyme product, wherein the first fermentation is yeast fermentation, the second fermentation is acetic acid bacteria fermentation and the third fermentation is lactic acid bacteria fermentation; and the sugar content of the enzyme product is less than 5 wt %, especially, in a predetermined fermentation condition, the sugar content of the enzyme product is less than 2.5 wt %.

8 Claims, No Drawings

METHOD FOR PRODUCING LOW-SUGAR VEGETABLE AND FRUIT ENZYME PRODUCT

BACKGROUND OF THE INVENTION

Field of the Invention

This invention relates to a fermentation technology, especially, it relates to a method for producing low-sugar vegetable and fruit enzyme product.

Description of the Related Art

Microbial fermentation technology is a technique in which a specific microorganism and a raw material are cultured together. In the past, the microbial fermentation technology was only applied to produce various types of fermented foods, such as cheese, yogurt, soy sauce, beer, or kimchi. With the advancement of biomedical technology, many studies have pointed out that the products that are metabolized or decomposed by microorganisms have benefits to living organisms, so microbial fermentation technology is beginning to be used to produce various types of enzyme products.

Although the enzyme products are considered to be beneficial to the human, such as promoting digestion and decomposing fat, in fact, the enzyme products made from the fruits and vegetables have a high sugar content. It means that the enzyme products contain more than 50% of the sugar. The reason is the fruits and vegetables are sweet, in particular, the sweetness of the fruit is higher, so using the fruits and vegetables as the materials for fermentation will let the enzyme products have a high sugar content.

The enzyme products with high-sugar are not only available to patients with metabolic syndrome or diabetes, but also increase risk of fatty liver, cancer, and obesity.

SUMMARY OF THE INVENTION

The main propose of this present invention is to provide a method for producing low-sugar vegetable and fruit enzyme product, which ferments the vegetable and fruit by at least three microbial fermentation stages to achieve the effect of reducing the sugar content of the final product.

The another propose of the present invention is to provide the method for producing low-sugar vegetable and fruit enzyme product, which can produce a large amount of low-sugar and high-fiber enzyme product to provide enzyme-related products. Therefore, the present invention discloses the method for producing low-sugar vegetable and fruit enzyme product which uses at least one vegetable and fruit as a material and then proceeds at least three fermentation stages to obtain a low-sugar enzyme product, wherein the bacterium of the first fermentation is yeast, such as *Saccharomyces cerevisiae*; the bacterium of the second fermentation is acetic acid bacteria, such as *Acetobacter aceti*; and the bacterium of the third fermentation is lactic acid bacteria, such as *Lactobacillus sporogenes*.

Furthermore, the method of this invention comprises the following steps:
a. preparing a starting medium including at least one vegetable and fruit, wherein the Brix value of starting material is from 15 to 25° Brix;
b. preparing an active yeast of *Saccharomyces cerevisiae* strain at a first inoculated amount of 0.01~1% w/v to mix with the starting material for anaerobic fermentation until the residual sugar content less than 2% and the alcohol content from 4.4 to 5.5%, so that a first fermented product is generated;
c. preparing an acetic acid bacteria of *Acetobacter aceti* strain at a second inoculated amount of 1~10% w/v to mix with the first fermented product for aerobic fermentation in 35~40° C. until the acetic acid concentration from 1.8 to 2.5%, so that a second fermented product is generated;
d. preparing a *Lactobacillus sporogenes* a third inoculated amount of 5~20% w/v to mix with the second fermented product for aerobic fermentation until the lactic acid content greater than 600 ppm and the sugar content less than 5%, so that a third fermented product is generated; and
e. filtering the third fermented product to obtain a low-sugar enzyme product.

In order to carry out the fermentation uniformly, each of the fermentation stages is in a stirring condition, wherein the stirring condition can be achieved by machine or hand.

In the step a, adding the sweeter enhancer, such as sugar, honey, brown sugar, molasses, into the starting medium can adjust the sugar content (Brix value) of the starting medium. And it can use HPLC to detecting the sugar content of the starting medium and then calculate the adding amount of the sweeter enhancer.

In the step b, the first inoculated amount can be 0.01, 0.02, 0.03, 0.05, 0.08, 0.1, 0.2, 0.3, 0.5, 0.6, 0.8, 0.9, 1.0% w/v. Preferably, the first inoculated amount is 0.1% w/v.

In the step c, the second inoculated amount can be 1, 2, 2.5, 3, 4, 5, 5.5, 6, 6.8, 7, 8, 8.5, 9, 10% w/v. Preferably, the second inoculated amount is 5% w/v. And the fermentation temperature of step b should be below 40° C.

In the step d, the third inoculated amount can be 5, 6, 6.5, 7, 8, 9, 10, 11, 11.5, 12, 12.3, 13, 14, 14.2, 15, 15.8, 16, 17, 17.6, 18, 19, 20% w/v. Preferably, the third inoculated amount is 5% w/v.

In one embodiment of the present invention, the vegetable and fruit can be citrus, *papaya*, pineapple, banana, kiwi, lime, lemon, grape etc., and when the weight of the vegetable and fruit is greater than or equal to 50% by the weight of starting medium, the sugar content of the low-sugar enzyme product is less than 2.5%.

In one embodiment of this invention, the Brix value of the second fermented product is lower than the Brix value of the first fermented product by at least about 10° Brix. In another embodiment of this invention, the acetic acid concentration of the second fermented product is greater than 2%.

In one embodiment of this invention, the alcohol content of the first fermented product is increased by at least 3% compared to that before fermentation, preferably greater than 4%.

In the other embodiment of this invention, the alcohol content of the second fermented product is less than 1%.

In one embodiment of this invention, the alcohol content of the third fermented product is less than 1%.

In another embodiment of this invention, the acetic acid concentration of the third fermented product is greater than 2%.

BRIEF DESCRIPTION OF THE DRAWINGS

None

DETAILED DESCRIPTION OF THE PREFERRED EMBODIMENTS

This present invention discloses a method for producing low-sugar vegetable and fruit enzyme product, which ferments a starting medium including at least one vegetable and fruit though multiple fermentation stages by different kinds of bacteria to generate an enzyme product having a low sugar content and multiple flavors. In other words, the method of this invention can ferment the fruits and vegetables with different sweetness to generate the enzyme product with less than 5% sugar content and the enzyme product has different acidity depending on the starting medium to bring consumers varied sourness and alcoholic flavors.

Moreover, the method or producing low-sugar vegetable and fruit enzyme product of this invention comprises at least three fermentation stages. The first fermentation stage is a yeast fermentation, for example, the strain of yeast is *Saccharomyces cerevisiae*; the second fermentation stage is a fermentation by acetic acid bacteria, for example, the strain of acetic acid bacteria is *Acetobacter aceti*; and the third fermentation stage is a fermentation by lactic acid bacteria, for example, the lactic acid bacteria is *Lactobacillus sporogenes*.

After proceeding the above three fermentation stages sequentially, and then filtering to remove the residuals, the low-sugar enzyme liquid can be obtained.

The method for analyzing the sugar content, the alcohol degree and the acidity by HPLC includes extracting or filtering the organic acid, the alcohol, the mono-disaccharide (monosaccharide and disaccharide) or the sugar alcohol from a sample, separating the extract or filtrate by HPLC column, detecting by the refractive index detector and UV-VIS detector, and then proceeding quantification by an external standard method. The organic acid comprises lactic acid, acetic acid, citric acid, tartaric acid, malic acid; mono-disaccharide and the sugar alcohol comprises glucose, fructose, sucrose, maltose, sorbitol and so on.

For example, the method for analyzing the sugar content, the alcohol degree and the acidity by HPLC used in the present invention is as following description:

First, taking 2.5 g of the standard sample of the alcohol or the organic acid, such as lactic acid and glacial acetic acid, is added to water until the total volume to 50 ml, the concentration is 50 mg/ml, and then analyzed by HPLC to detecting the retention time of the standard sample. Adding 5 ml of the enzyme liquid to water until the total volume is 10 ml, centrifuging at 4000 rpm for 5 minutes at 25° C., collecting and filtering the supernatant, and then analyzed by HPLC. Finally, it can obtain the organic acid content or the alcohol content of the enzyme solution by external standard method.

The HPLC analysis conditions of organic acid and alcohol are: IC Sep ICE-Coregel 87H3, mobile phase 25 mM: sulfuric acid, flow rate: 0.5 ml/min, temperature: 40° C., injection volume: 20 µl, analysis time: 40 minutes. The Refractive Index Detector is used for detecting alcohol, and the UV-VIS detector or RI detector is used for detecting organic acid.

The HPLC conditions of the mono-disaccharide were: YMC-Pack polyamine II, 250×4.6 mm ID, Particle size: 5 µm, mobile phase: acetonitrile/water (750 ml/250 ml), flow rate of 0.7 ml/min, temperature: 25° C., the injection volume: 20 µl, the analysis time: 60 minutes, and the detecting instrument is RI detector.

Hereinafter, in order to further illustrate the present invention, an embodiment will be described in detail as follows.

The method for producing low-sugar vegetable and fruit enzyme product in one embodiment of this invention comprises:

Step 101: Preparation Starting Medium

Took a selected vegetable and fruit, after washing, cut, crushed and poured the selected vegetable and fruit, proceeded enzyme hydrolysis, such as gelatinase, cellulolytic enzyme, or any hydrolyzed enzyme known to an ordinary person skilled in the art, and then adjusted the sugar content by adding a sugar to obtain a starting medium in which the Brix value was 20° Brix and the total amount of the mono-disaccharide was 14%.

Furthermore, after hydrolysis, the total amount of the mono-disaccharide can be detected by HPLC, and then calculated the adding amount of sugar by the following formula:

The adding amount of sugar=[total weight of raw material×(0.14−the mono-disaccharide content of the raw material(%))]÷0.86

Step 102: Yeast Fermentation Stage

The yeast is *Saccharomyces cerevisiae*, the inoculated amount was 0.1% w/v (the effective number of bacteria: $10^9$ CFU), for example, 500 L of vegetable and fruit juice required 500 mL of yeast liquid. In this stage, it was anaerobic fermentation, the stirring rate was 50 rpm, and the fermentation temperature was 28° C. On the fifth day of the yeast fermentation stage, the residual sugar content and the alcohol content of the fermentation product were detected by HPLC, when the residual sugar content was less than 2% and the alcohol content was between 4.5 to 5.5%, the yeast fermentation stage completed to obtain a first fermentation product. The first fermented product was used for proceeding the next stage for the acetic acid fermentation.

Detected the first fermented product from different kind vegetables and fruits by HPLC, the results were shown in Table 1.

TABLE 1 the results of detecting the pH value, the total mono-disaccharide content and the alcohol content of each of the first fermentation products by HPLC

| Material | pH value | mono-disaccharide content (%) | alcohol content (%) |
|---|---|---|---|
| Citrus | 3.22 ± 0.07 | 0.50 ± 0.16 | 4.73 ± 0.03 |
| Papaya | 3.55 ± 0.35 | 0.63 ± 0.09 | 4.57 ± 0.04 |
| Pineapple | 3.29 ± 0.25 | 0.38 ± 0.13 | 4.68 ± 0.04 |
| Banana | 4.36 ± 0.41 | 0.33 ± 0.12 | 4.92 ± 0.04 |
| Green plum | 3.07 ± 0.15 | 0.25 ± 0.02 | 4.99 ± 0.03 |
| Noni | 3.72 ± 0.19 | 0.78 ± 0.11 | 4.58 ± 0.04 |
| Lemon peel | 2.91 ± 0.18 | 0.69 ± 0.08 | 4.66 ± 0.03 |
| Grapefruit | 3.93 ± 0.17 | 0.17 ± 0.09 | 5.13 ± 0.05 |
| Kiwifruit | 3.56 ± 0.13 | 0.23 ± 0.12 | 5.08 ± 0.03 |
| Lyme | 2.99 ± 0.20 | 0.56 ± 0.12 | 4.76 ± 0.03 |
| Grape | 3.70 ± 0.33 | 0.66 ± 0.04 | 4.68 ± 0.04 |

Step 103: Acetic Acid Fermentation Stage

In detail, *Acetobacter aceti* was mixed with the first fermented product for aerobic fermentation, wherein the inoculated amount was 5% w/v (the effective number of bacteria: $10^8$ CFU), the aeration was about 0.5 VVM, the stirring rate was about 200 rpm, the fermentation temperature must be controlled at 37° C. and must not be higher than 40° C., 48 hours. When the acetic acid concentration was between 1.8% to 2.5%, the acetic acid fermentation stage completed and a second fermented product was obtained, wherein the acetic acid concentration of the second fermented product was between 1.8% to 2.5%.

Detected the second fermented product by HPLC, the results were shown in Table 2.

TABLE 2 the results of detecting the pH value, the total mono-
disaccharide content and the acetic acid content of
each of the second fermentation products by HPLC

| Material | pH value | mono-disaccharide content (%) | acetic acid content (%) |
|---|---|---|---|
| Citrus | 3.03 ± 0.10 | 0.21 ± 0.09 | 0.16 ± 0.05 |
| Papaya | 3.27 ± 0.18 | 0.27 ± 0.12 | 0.33 ± 0.04 |
| Pineapple | 3.13 ± 0.11 | 0.16 ± 0.07 | 0.21 ± 0.03 |
| Banana | 3.33 ± 0.19 | 0.19 ± 0.08 | 0.27 ± 0.04 |
| Green plum | 2.99 ± 0.06 | 0.15 ± 0.06 | 0.09 ± 0.03 |
| Noni | 3.51 ± 0.28 | 0.47 ± 0.08 | 0.05 ± 0.02 |
| Lemon peel | 2.87 ± 0.19 | 0.29 ± 0.16 | 0.11 ± 0.02 |
| Grapefruit | 3.58 ± 0.26 | 0.09 ± 0.03 | 0.25 ± 0.04 |
| Kiwifruit | 3.36 ± 0.20 | 0.10 ± 0.02 | 0.46 ± 0.04 |
| Lyme | 2.88 ± 0.16 | 0.35 ± 0.09 | 0.23 ± 0.01 |
| Grape | 3.33 ± 0.26 | 0.47 ± 0.17 | 0.28 ± 0.06 |

Step 4: Lactic Acid Fermentation Stage

*Lactobacillus sporogenes* was mixed with the second fermented product for aerobic fermentation, wherein the inoculated amount was 5% w/v (the effective number of bacteria: $10^8$ CFU), the aeration was about 0.5 VVM, the stirring rate was about 300 rpm, the fermentation temperature was at 35° C. When the fermentation time reached to 72 hours, detecting the lactic acid content by HPLC, if the lactic acid content greater than 600 ppm, it mean that the lactic acid fermentation stage completed and a third fermented product was obtained, wherein the sugar content of the third was less than 5%.

Detected the third fermented product by HPLC, the results were shown in Table 3.

TABLE 3 the results of detecting the pH value, the total mono-disaccharide content, the acetic acid
content and the lactic acid content of each of the third fermentation products by HPLC

| Material | pH value | mono-disaccharide content (%) | alcohol content (%) | acetic acid content (%) | lactic acid content (ppm) |
|---|---|---|---|---|---|
| Citrus | 3.19 ± 0.02 | 0.13 ± 0.03 | 0.14 ± 0.06 | 2.06 ± 0.08 | 739 |
| Papaya | 3.20 ± 0.10 | 0.19 ± 0.11 | 0.27 ± 0.06 | 2.12 ± 0.06 | 818 |
| Pineapple | 3.19 ± 0.07 | 0.20 ± 0.09 | 0.18 ± 0.03 | 1.95 ± 0.06 | 784 |
| Banana | 3.21 ± 0.14 | 0.18 ± 0.09 | 0.13 ± 0.06 | 1.99 ± 0.02 | 889 |
| Green plum | 3.09 ± 0.05 | 0.17 ± 0.09 | 0.06% ± 0.03 | 2.14 ± 0.07 | 816 |
| Noni | 3.33 ± 0.06 | 0.18 ± 0.06 | 0.05 ± 0.03 | 1.93 ± 0.05 | 650 |
| Lemon peel | 3.25 ± 0.13 | 0.21 ± 0.09 | 0.08 ± 0.03 | 2.00 ± 0.03 | 661 |
| Grapefruit | 3.30 ± 0.17 | 0.16 ± 0.06 | 0.09 ± 0.03 | 2.07 ± 0.08 | 735 |
| Kiwifruit | 3.29 ± 0.08 | 0.12 ± 0.08 | 0.20 ± 0.04 | 2.18 ± 0.04 | 833 |
| Lyme | 3.17 ± 0.14 | 0.13 ± 0.08 | 0.15 ± 0.02 | 2.11 ± 0.06 | 726 |
| Grape | 3.31 ± 0.15 | 0.27 ± 0.09 | 0.15 ± 0.04 | 2.00 ± 0.02 | 713 |

Step 105: Separation and Filtration

Removed the residuals from the third fermented product to obtain an enzyme liquid which has a sugar content less than 5%.

According to the above description, the method disclosed by the present invention can produce the low-sugar enzyme liquid effectively, and the sugar content of the low-sugar enzyme liquid is less than ⅓ of the sugar content of the starting medium or the vegetable and fruit thereof. Furthermore, the low-sugar enzyme liquid can be mixed with other edible ingredients or/and probiotics to form an enzyme-related product.

Taking different vegetable and fruit and combination thereof to be the material of the starting medium, it was used to produce the low-sugar enzyme liquids by the method of this invention, wherein if there has more two kinds vegetable and fruit in the starting medium, each vegetable and fruit has the same weight to each other. Detecting the PH values of the fermented products from different vegetable and fruit in each fermentation stage and analyzing the sugar content, alcoholic content and acidic content of each low-sugar enzyme liquid by HPLC, the results were shown in Tables 4 to 9, wherein "ND" means "no detecting".

TABLE 4

The results of detecting PH values of the fermented products
from different vegetable and fruit in each fermentation stage

| | pH | | |
|---|---|---|---|
| Material | Yeast fermentation | Acetic acid fermentation | Lactic acid fermentation |
| Citrus | 3.22 ± 0.07 | 3.03 ± 0.10 | 3.19 ± 0.02 |
| Papaya | 3.55 ± 0.35 | 3.27 ± 0.18 | 3.20 ± 0.10 |
| Pineapple | 3.29 ± 0.25 | 3.13 ± 0.11 | 3.19 ± 0.07 |
| Banana | 4.36 ± 0.41 | 3.33 ± 0.19 | 3.21 ± 0.14 |
| Green plum | 3.07 ± 0.15 | 2.99 ± 0.06 | 3.09 ± 0.05 |
| integrated fruits and vegetables | 3.66 ± 0.31 | 3.25 ± 0.22 | 3.14 ± 0.11 |
| Noni | 3.72 ± 0.19 | 3.51 ± 0.28 | 3.33 ± 0.06 |
| Lemon peel | 2.91 ± 0.18 | 2.87 ± 0.19 | 3.25 ± 0.13 |
| Grapefruit | 3.93 ± 0.17 | 3.58 ± 0.26 | 3.30 ± 0.17 |
| Kiwifruit | 3.56 ± 0.13 | 3.36 ± 0.20 | 3.29 ± 0.08 |
| Lyme | 2.99 ± 0.20 | 2.88 ± 0.16 | 3.17 ± 0.14 |
| Grape | 3.70 ± 0.33 | 3.33 ± 0.26 | 3.31 ± 0.15 |
| Citrus + Papaya | 3.43 ± 0.26 | 3.29 ± 0.21 | 3.14 ± 0.18 |
| Pineapple + Papaya | 3.46 ± 0.28 | 3.21 ± 0.27 | 3.25 ± 0.19 |
| Apple + Grape | 3.56 ± 0.15 | 3.32 ± 0.26 | 3.21 ± 0.09 |

TABLE 5

The results of analyzing the mono-disaccharide
of low-sugar enzyme liquids by HPLC

| Material | glucose peak area | fructose peak area | sucrose peak area | maltose peak area |
|---|---|---|---|---|
| Citrus | 167049 | 571974 | 292417 | ND |
| Papaya | 1251 | 24899 | 6809 | ND |
| Pineapple | 3290856 | 810756 | 234246 | 146032 |
| Banana | 78910 | 3311304 | ND | 187114 |
| Green plum | 2906656 | 7150972 | 41509 | ND |
| Apple | 673682 | 803153 | ND | ND |
| Noni | 4521548 | 6529105 | 236675 | ND |
| Lemon peel | 6153940 | 175436 | 48770 | 111832 |
| Grapefruit | 4126207 | 3811315 | 85754 | 41796 |
| Kiwifruit | 95106 | 16552 | 10303 | ND |
| Lyme | 807997 | 3179945 | 78320 | 265166 |

TABLE 5-continued

The results of analyzing the mono-disaccharide
of low-sugar enzyme liquids by HPLC

| Material | glucose peak area | fructose peak area | sucrose peak area | maltose peak area |
|---|---|---|---|---|
| Grape | 23454 | ND | 5840 | 36910 |
| Citrus + Papaya | 1442478 | 2556770 | 122301 | ND |
| Pineapple + Papaya | 650197 | 1041840 | 414256 | ND |
| Apple + Grape | 3938028 | 3765795 | ND | 43024 |

TABLE 6

The results of analyzing the sugar content
of low-sugar enzyme liquids by HPLC

| Material | glucose (g/100 ml) | fructose (g/100 ml) | sucros (g/100 ml) | maltose (g/100 ml) | Total |
|---|---|---|---|---|---|
| Citrus | 0.08 | 0.2 | 0.10 | ND | 0.38 |
| Papaya | 0.00 | 0.01 | 0.001 | ND | 0.01 |
| Pineapple | 1.61 | 0.28 | 0.078 | 0.08 | 2.05 |
| Banana | 0.04 | 1.15 | ND | 0.10 | 1.30 |
| Green plum | 1.42 | 2.49 | 0.013 | ND | 3.92 |
| Apple | 0.33 | 0.28 | ND | ND | 0.61 |
| Noni | 2.21 | 2.27 | 0.078 | ND | 4.56 |
| Lemon peel | 3.01 | 0.06 | 0.015 | 0.06 | 3.14 |
| Grapefruit | 2.02 | 1.33 | 0.028 | 0.02 | 3.40 |
| Kiwifruit | 0.05 | 0.00 | 0.003 | ND | 0.06 |
| Lyme | 0.40 | 1.11 | 0.025 | 0.15 | 1.67 |
| Grape | 0.01 | ND | 0.001 | 0.02 | 0.04 |
| Citrus + Papaya | 0.71 | 0.9 | 0.04 | ND | 1.64 |
| Pineapple + Papaya | 0.32 | 0.36 | 0.138 | ND | 0.82 |
| Apple + Grape | 1.93 | 1.31 | ND | 0.03 | 3.26 |

TABLE 7

The results of analyzing the acids of low-sugar enzyme liquids by HPLC

| Material | Lactic acid peak area | Acetic acid peak area | Citric acid peak area | Tartaric acid peak area | Malic acid peak area |
|---|---|---|---|---|---|
| Citrus | ND | 529726 | 1448716 | 1940058 | 2013390 |
| Papaya | 3718750 | 779378 | ND | 1117820 | ND |
| Pineapple | 6188896 | 4885190 | ND | 418014.00 | ND |
| Banana | 19436 | 329834 | 19963546 | 83390.00 | ND |
| Green plum | ND | 486462 | 20616528 | ND | ND |
| integrated fruits and vegetables | 7752606 | 2015102 | ND | 1578966 | ND |
| Noni | 201316 | 936066 | ND | 3689178 | ND |
| Lemon peel | 3969852 | 2370434 | ND | 949784.00 | ND |
| Grapefruit | 228340 | 147746 | ND | 1603482.00 | ND |
| Kiwifruit | ND | 174810 | 5607618 | 3924690 | 3776624 |
| Lyme | ND | 548492 | 16337486 | ND | ND |
| Grape | 1097013 | 314349 | ND | 1275058.00 | ND |
| Citrus + Papaya | 5862450 | 1658201 | ND | ND | ND |
| Pineapple + Papaya | 4531688 | 3325652 | ND | 2297708 | ND |
| Apple + Grape | 1851425 | 134846 | ND | 1989364.00 | ND |

TABLE 8

The results of analyzing the acidic content of low-sugar enzyme liquids by HPLC

| Material | Lactic acid (g/100 ml) | Acetic acid (g/100 ml) | Citric acid (g/100 ml) | Tartaric acid (g/100 ml) | Malic acid (g/100 ml) | Total |
|---|---|---|---|---|---|---|
| Citrus | ND | 0.16 | 0.251 | 0.31 | 0.36 | 1.1 |
| Papaya | 1.0 | 0.23 | ND | 0.18 | ND | 1.4 |
| Pineapple | 1.6 | 1.44 | ND | 0.06 | ND | 3.1 |
| Banana | 0.0 | 0.10 | 3.544 | 0.01 | ND | 3.7 |
| Green plum | ND | 0.14 | 3.66 | ND | ND | 3.8 |
| integrated fruits and vegetables | 2.0 | 0.59 | ND | 0.25 | ND | 2.8 |
| Noni | 0.1 | 0.28 | ND | 0.58 | ND | 0.9 |
| Lemon peel | 1.0 | 0.70 | ND | 0.15 | ND | 1.9 |
| Grapefruit | 0.1 | 0.04 | ND | 0.25 | ND | 0.4 |
| Kiwifruit | ND | 0.05 | 0.991 | 0.62 | 0.68 | 2.3 |
| Lyme | ND | 0.16 | 2.899 | ND | ND | 3.1 |
| Grape | 0.3 | 0.09 | ND | 0.20 | ND | 0.6 |
| Citrus + Papaya | 1.5 | 0.49 | ND | ND | ND | 2.0 |
| Pineapple + Papaya | 1.2 | 0.98 | ND | 0.36 | ND | 0.43 |
| Apple + Grape | 0.5 | 0.04 | ND | 0.31 | ND | 0.8 |

TABLE 9

The results of analyzing the alcohol content
of low-sugar enzyme liquids by HPLC

| Material | alcohol peak area | alcohol content %(v/v) |
|---|---|---|
| Citrus | 10629776 | 5.30 |
| Papaya | 1361298 | 0.67 |
| Pineapple | 4934164 | 2.45 |
| Banana | 9662420 | 4.82 |
| Green plum | 12821388 | 6.40 |
| Apple | 4621235 | 2.30 |
| Noni | 662342 | 0.32 |
| Lemon peel | 6377260 | 3.18 |
| Grapefruit | 5955699 | 2.96 |
| Kiwifruit | 12085396 | 6.03 |
| Lyme | 6865895 | 3.42 |
| Grape | 14868288 | 7.42 |
| Citrus + Papaya | 9982450 | 4.98 |
| Pineapple + Papaya | 6686036 | 3.33 |
| Apple + Grape | 701355 | 0.34 |

According to Tables 5 to 9, it shows that the method of the present invention can ferment different kinds of vegetables and fruits to produce the low-sugar enzyme liquids, and the low-sugar enzyme liquids have different flavors depending on the composition of the starting medium.

Moreover, comparing the sugar content of the low-sugar enzyme liquid of the present invention (hereafter referred to as "the enzyme liquid of the invention") and the commercial enzyme liquids, the result was shown in Table 10, wherein the starting medium used for the enzyme liquid of the invention includes citrus, *papaya*, pineapple, banana, kiwifruit, Lyme, grape, or a combination of any two kinds vegetable and fruit and the weight of the vegetables and fruits is greater than or equal to 50% of the weight of the starting medium.

TABLE 10

Comparing result of sugar content of the enzyme liquid of the invention and commercial enzyme liquids

| | The invention | Commercial product 1 | Commercial product 2 | Commercial product 3 | Commercial product 4 | Commercial product 5 | Commercial product 6 |
|---|---|---|---|---|---|---|---|
| mono-disaccharide content (g/100 g) | <2.5 | 60.57 | 64.48 | 35.28 | 59.03 | 49.0 | 67.18 |

According to the result of Table 10, it shows that the method for producing low-sugar vegetable and fruit enzyme product of the invention can effectively reduce the sugar content of the enzyme liquid.

What is claimed is:

1. A method for producing low-sugar vegetable and fruit enzyme product, consisting of:
   a. preparing a starting medium including at least one vegetable and fruit, adding a sugar to obtain the starting medium with 15 to 25° Brix;
   b. preparing an active yeast of *Saccharomyces cerevisiae* strain at a first inoculated amount of 0.01~1% w/v to mix with the starting medium for anaerobic fermentation until a residual sugar content is less than 2% and an alcohol content is from 4.4 to 5.5%, so that a first fermented product is generated;
   c. preparing an acetic acid bacteria of *Acetobacter aceti* strain at a second inoculated amount of 1~10% w/v to mix with the first fermented product for aerobic fermentation in 35~40° C. until an acetic acid concentration is from 0.05 to 0.46%, so that a second fermented product is generated;
   d. preparing a *Lactobacillus sporogenes* at a third inoculated amount of 5~20% w/v to mix with the second fermented product for aerobic fermentation until a lactic acid content is greater than 600 ppm and a content of total sugar including both the added sugar in step a and the residual sugar is less than 2.5%, so that a third fermented product is generated; and
   e. filtering the third fermented product to obtain the low-sugar vegetable and fruit enzyme product.

2. The method of claim 1, wherein the fruit is selecting from a group consisting of citrus, papaya, pineapple, banana, kiwi, lime, lemon and grape.

3. The method of claim 2, wherein when a weight of the vegetable and fruit is greater than or equal to 50% by a weight of the starting medium, the sugar content of the low-sugar enzyme product is less than 2.5%.

4. The method of claim 1, wherein the Brix value of the second fermented product is lower than the Brix value of the first fermented product by at least about 10° Brix.

5. The method of claim 1, wherein the alcohol content of the first fermented product is increased by at least 3% compared to that before fermentation.

6. The method of claim 1, wherein the alcohol content of the second fermented product is less than 1%.

7. The method of claim 1, wherein the alcohol content of the third fermented product is less than 1%.

8. The method of claim 1, wherein the acetic acid concentration of the third fermented product is greater than 2%.

* * * * *